US006382970B1

(12) United States Patent
Foster

(10) Patent No.: US 6,382,970 B1
(45) Date of Patent: May 7, 2002

(54) DENTAL AIR/WATER SYRINGE PURGE DEVICE

(76) Inventor: Stephen A. Foster, 5300 109N, Lebanon, TN (US) 37087

( * ) Notice: Subject to any disclaimer, the term of this patent is extended or adjusted under 35 U.S.C. 154(b) by 0 days.

(21) Appl. No.: 09/766,374

(22) Filed: Jan. 19, 2001

(51) Int. Cl.$^7$ ................................................ A61C 17/02
(52) U.S. Cl. ....................................................... 433/80
(58) Field of Search .................................. 433/80, 104

(56) References Cited

U.S. PATENT DOCUMENTS

| 4,902,225 A | 2/1990 | Lohn ........................... 433/80 |
| 4,957,483 A | 9/1990 | Gonser et al. ................ 604/30 |
| 5,199,871 A | 4/1993 | Young ......................... 433/80 |
| 5,286,201 A | 2/1994 | Yu ............................... 433/80 |
| 5,376,003 A | 12/1994 | Rizkalla ..................... 433/116 |
| 5,378,149 A | 1/1995 | Stropko ....................... 433/80 |
| 5,547,374 A | 8/1996 | Coleman ..................... 433/85 |
| 5,658,144 A | 8/1997 | Tinder et al. ................ 433/80 |
| D409,305 S | 5/1999 | Martin et al. ................ 24/113 |
| 5,908,296 A | 6/1999 | Kipke et al. ................ 433/80 |

*Primary Examiner*—Cary E. O'Connor
(74) *Attorney, Agent, or Firm*—Waddey & Patterson; Wayne Beavers; Guy W. Hensley

(57) ABSTRACT

A dental air/water syringe purge hold-down device having a hold-down portion, a bracing portion and one or more connecting portions. The hold-down portion holds down one or more buttons on a dental syringe. The bracing portion stably holds the hold-down portion against the buttons on the syringe and the side members serve to connect the hold-down portion and the bracing portion and enhance the hold-down activity of the hold-down portion.

24 Claims, 5 Drawing Sheets

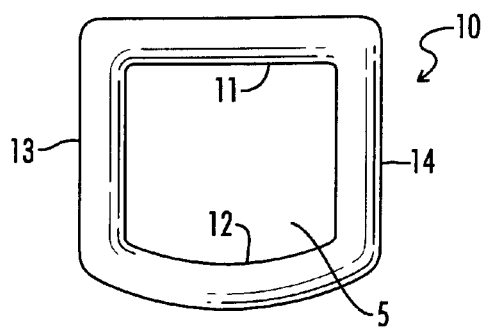
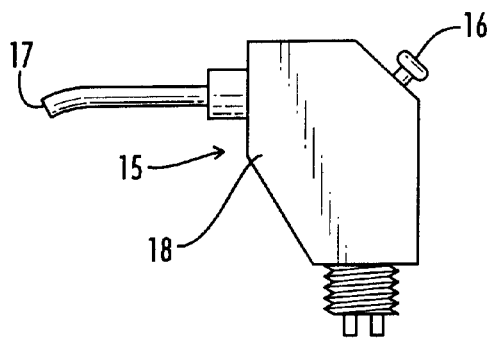
FIG. 1
FIG. 2
*(PRIOR ART)*
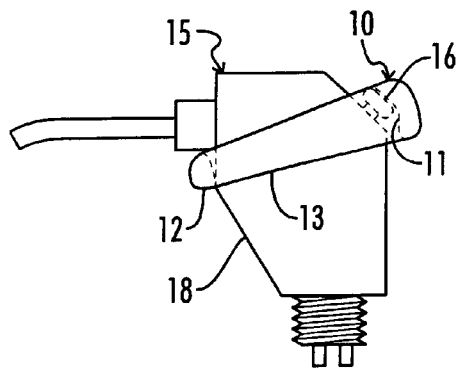
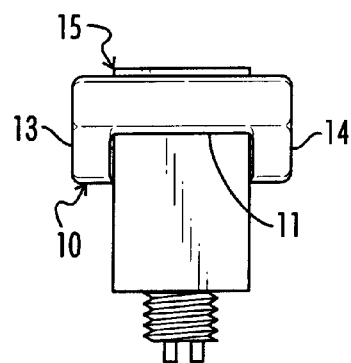
FIG. 3
FIG. 4
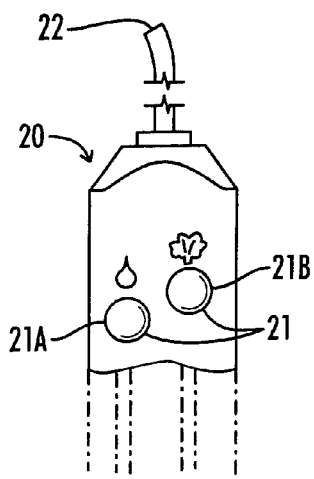
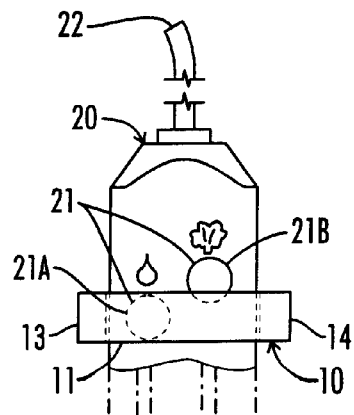
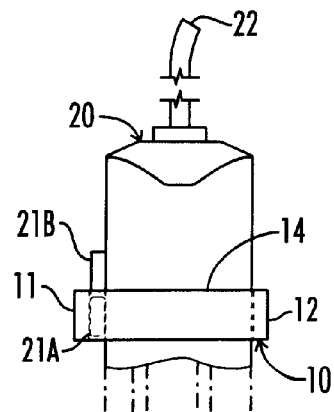
FIG. 5
*(PRIOR ART)*
FIG. 6
FIG. 7

DENTAL AIR/WATER SYRINGE PURGE DEVICE

BACKGROUND OF THE INVENTION

This invention relates to a device to aid in purging the water lines in dental syringes. The device continually depresses the buttons on the syringe to allow one to purge the water line of the syringe without having to manually perform the task.

It is known in the practice of dentistry and orthodontia to employ syringes to apply air and/or water to the mouth of a patient during treatment. Known dental syringes often employ air and water so that an operator of such a syringe may use compressed air or a stream of water by depressing the air and water buttons respectively, or a spray of water by depressing both buttons simultaneously.

While there are no known health risks related to the air lines of dental air/water syringes, there is potential for water line contamination when using the water lines of such syringes. Water lines of dental syringes either use self-contained (i.e., bottled) water, or non-self-contained water from sources such as municipalities or wells. Systems using bottled water are disinfected by first purging the water lines with a disinfectant solution, then by purging the disinfectant from the water lines with the non-self-contained water. Water lines connected to municipal and other non-self-contained water sources need only be purged with the water; no additional disinfectant is normally used. Regardless of which water source is used, the possibility of water line contamination exists. Such contamination is due to a condition called "biofilm." Biofilm is the accumulation of bacterial-laden slime inside water lines having a small diameter. Biofilm releases bacteria into the water inside the small diameter water lines inside dental units. There is a potential for patient exposure to bacterially-contaminated water from biofilm inside dental unit water lines.

To lessen the risk of patient exposure to water-borne bacteria from dental units contaminated with biofilm, The Centers for Disease Control and Prevention (CDC) recommends purging dental unit water lines at least three (3) minutes at the beginning of each day of use, and at least twenty (20) seconds between patients. The longer a line is purged, the safer the water is from becoming infected.

While it is known to purge dental syringes by depressing the water button or both the air and water buttons by hand, holding down a syringe button to purge the water line in accordance with CDC recommendations is physically demanding, and if not performed properly, is a potential health hazard. Moreover, such a task is also time-consuming if performed properly. These and other problems are effectively addressed by the instant invention.

Although numerous patents have been issued on various features of dental syringes, there is no device that holds down the buttons on a dental syringe to properly purge water lines. Such is the purview of the instant invention.

SUMMARY OF THE INVENTION

The present invention incorporates a portion that holds down the water button, or air button, or both, on a dental air/water syringe. This so-called "hold-down portion" is forced against the water button, air button, or both, to continually depress said button or buttons, by a portion that is called a "bracing portion." In addition to causing continual depression of the buttons by the hold-down portion, the bracing portion adds stability to the apparatus while it is being used in combination with the syringe.

In light of the need for a device to purge the water lines of a dental syringe in a predictable, uniform, and continuous manner, it is an object of the instant invention to provide a syringe purge device that holds down one or buttons on a syringe, eliminating the need for constant supervision or human involvement.

It is a further object of the invention to enable a dental syringe user to purge the syringe water line in accordance with health recommendations or regulations.

It is a further object of the invention to lessen the stress of purging a dental syringe water line on the hand of the user of such a syringe.

It is a further object of the invention to provide a device that will save time in purging a dental syringe water line by eliminating the need to constantly attend a dental syringe during a water line purging process.

In addition to the foregoing, further objects, features, and advantages of the present invention should become more readily apparent to those skilled in the art upon a reading of the following detailed description in conjunction with the drawings, wherein there are shown and described illustrated embodiments of the invention.

BRIEF DESCRIPTION OF THE DRAWINGS

FIG. 1 is a top view of a syringe purge device comprising a loop having a flattened portion for holding down syringe buttons, a bracing portion for stably biasing the hold-down portion against the syringe buttons, and two side portions connecting the hold-down portion and the bracing portion.

FIG. 2 is a side view of a standard dental syringe.

FIG. 3 is a side view of a standard dental syringe in combination with the device of FIG. 1.

FIG. 4 is an operator's view of the standard syringe and device combination of FIG. 3.

FIG. 5 is a top view of a euro-style syringe having buttons for dispensing air and water.

FIG. 6 is a top view of a euro-style syringe in combination with the device of FIG. 1.

FIG. 7 is a side view of FIG. 6.

DESCRIPTION OF THE PREFERRED EMBODIMENTS

Figure 8:
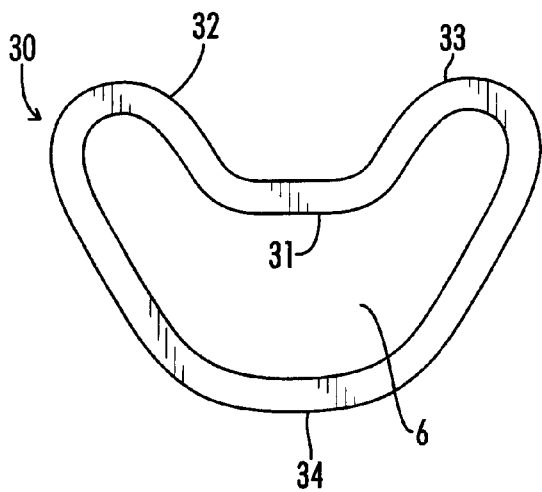
FIG. 8 is a top view of an inverted A-shaped syringe purge loop.

Referring to FIG. 1, the hold-down device 10 is comprised of a hold-down portion 11 for holding down at least one of the buttons on a dental syringe, a bracing portion 12 for holding the hold-down portion 11 against the syringe button, and two connecting members 13 and 14 for structurally connecting the hold-down portion 11 with the bracing portion 12. Hold-down portion 11, bracing portion 12, and connecting members 13 and 14 define an opening 5 which will be substantially filled by a dental air/water syringe when hold-down device 10 is installed as described below.

Hold-down device 10 is preferably made of a one-piece construction, although the device could be made of more than one piece in an alternate design, still achieving the goals of the instant invention. Additionally, hold-down device 10 is preferably made of plastic, even though other materials that accomplish the same goals would suffice. Materials that would be suitable in malting the present invention include Selcon®, Delrin®, Ploypropylene, Polycarbonate, and rigid PVC plastic. In addition to the foregoing materials listed, any material that accomplishes the goals of the invention herein described or known in the art is considered an equivalent material. Any material that is used in a preferred embodiment of hold-down device 10 should be semi-rigid. In the context of this patent, "semi-rigid" means that hold-down device 10 simultaneously has (a)sufficient flexibility for hold-down portion 11 and bracing portion 12 to be placed around the head of a dental air/water syringe and perform the holding down of the desired buttons, while at the same time having (b)sufficient rigidity for connecting members 13 and 14 to connect hold-down portion 11 to bracing portion 12 without allowing either the apparatus to slip off the syringe or allowing hold-down device 10 to fail to achieve the button-depressing functions described above.

The dimensions of hold-down device 10 are also included in FIG. 1, but such dimensions are merely illustrative of the size of one embodiment. Variations in the dimensions of hold-down device 10 should be made where necessary to allow hold-down device 10 to achieve the objects of the invention herein described.

FIG. 2 depicts a typical prior art standard dental syringe 15 including at least one button 16 for dispensing water and/or air from syringe tip 17. FIGS. 3 and 4 show syringe 15 with hold-down device 10 installed. Hold-down device 10 is featured in combination with syringe 15 such that hold-down portion 11 continually depresses button 16 on syringe 15. Bracing portion 12 is set against forward area 18 of syringe 15 so as to hold the hold-down portion 11 against button 16 on syringe 15, and connecting members 13 and 14 structurally support bracing portion 12 in place, and force hold-down portion 11 against button 16 on syringe 15. Hold-down portion 11 may alternatively be flat or multi-surfaced, or it may have a groove or other means on its inner surface to secure it against movement while it is in place and depressing button 16 of syringe 15.

The installation of hold-down device 10 on syringe 15 is preferably performed by inserting syringe 15 forwardly through opening 5 in hold-down device 10, setting bracing portion 12 against forward area 18 of syringe 15, and installing hold-down portion 11 securely against button 16. When hold-down device 10 is installed on syringe 15 as shown, the user would not need to attend the combination, but would be free to perform other tasks during purging.

FIG. 5 shows another major style of dental syringe 20, called a "euro-style syringe," which includes buttons 21A and 21B controlling the discharge of water and air, respectively, from syringe tip 22 of syringe 20. Euro-style syringes are distinguished from standard syringes by offset water and air buttons 21A and 21B, and by the characteristic of discharging water and/or air more or less parallel to their water and air lines, versus the perpendicular discharge of standard syringes. These two structural distinctions cause particular difficulty when using the syringe in combination with hold-down device 10, as is seen below.

Referring to FIGS. 6 and 7, hold-down device 10 is featured in combination with euro-style syringe 20 such that hold-down portion 11 depresses at least one of buttons 21A and 21B on syringe 20 to control the discharge of water and air, respectively, from syringe tip 22 of syringe 20. Hold-down device 10 further comprises a bracing portion 12 forcing hold-down portion 11 against at least one of buttons 21A and 21B of syringe 20. Connecting members 13 and 14 structurally connect hold-down portion 11 to bracing portion 12. The length of connecting members 13 and 14 is such that hold-down portion 11 and bracing portion 12 act to hold down at least one of buttons 21A and 21B as described above. There should be inherent flexibility in hold-down portion 11 and bracing portion 12 to bias hold-down portion 11 against one or more of buttons 21A and 21B of syringe 20.

The hold-down device 10 of FIG. 1 could alternatively be described as being a loop having a flattened hold-down portion 11 for holding down one or more buttons on a standard dental syringe 15 as in FIGS. 3 and 4, or for holding down one or more buttons on a euro-style syringe 20 as in FIGS. 6 and 7. Hold-down device 10 can further be characterized as having a bracing portion 12 that holds hold-down portion 11 against one or more buttons on a standard dental syringe 15 as in FIGS. 3 and 4, or against one or more buttons on a euro-style syringe 20 as in FIGS. 6 and 7. Bracing portion 12 provides stability to the combination of the hold-down device and the syringe of choice in that, once installed, its connecting function is performed continuously so that hold-down portion 11 will not spontaneously disengage the syringe buttons once in place on the syringe.

Hold-down device 10 is preferably installed on syringe 20 by inserting syringe tip 22 forwardly through opening 5 in hold-down device 10, then simultaneously securing bracing portion 12 and hold-down portion 11 around syringe 20 so that hold-down portion 11 holds down at least one of buttons 21A and 21B on syringe 20. When hold-down device 10 is installed on syringe 20 as shown, the user would not need to attend the combination, but would be free to perform other tasks during purging.

One of the problems inherent to the embodiment of hold-down device 10 is that it often has a tendency to slip off the buttons of euro-style syringe 20. Additionally, due to insufficient biasing of hold-down portion 11, hold-down device 10 typically has difficulty continuously holding down buttons on both types of syringes 10 and 20. A second embodiment, depicted at FIG. 8 and enabled below, was devised to overcome these difficulties.

FIG. 8 illustrates a preferred embodiment of hold-down device 30. Hold-down device 30 comprises an endless semi-rigid flexible loop having a flattened portion 31, biasing wings 32 and 33, and a vertex 34 in the part of the loop opposite flattened portion 31. Biasing wings 32 and 33 of extend as part of the loop away from flattened portion 31 such that biasing wings 32 and 33 serve as flexible springs, forcing flattened portion 31 against one or more buttons 21A and 21B on a euro-style syringe as in FIGS. 10 and 11, or against one or more buttons 36A and 36B on a standard dental syringe as in FIGS. 9 and 12.

Biasing wings 32 and 33 of hold-down device 30 (FIG. 8) may be distinguished from connecting members 13 and 14 of device 10 (FIG. 1) in that biasing wings 32 and 33 have the improved biasing function in addition to the connecting function served by all of wings 32 and 33 and connecting members 13 and 14.

Hold-down device 30 is preferably made of a single molded construction and is preferably made of plastic. The device could also be made from acrylic or from other types of materials as discussed hereinabove. Other types of semi-rigid materials may be used as are known in the art, but the indispensable characteristic of hold-down device 30 is that the hold-down device will preferably strike a balance between rigidity and flexibility so as to be able to be placed on, remain in place on, and hold down buttons on a dental syringe.

Figure 10:
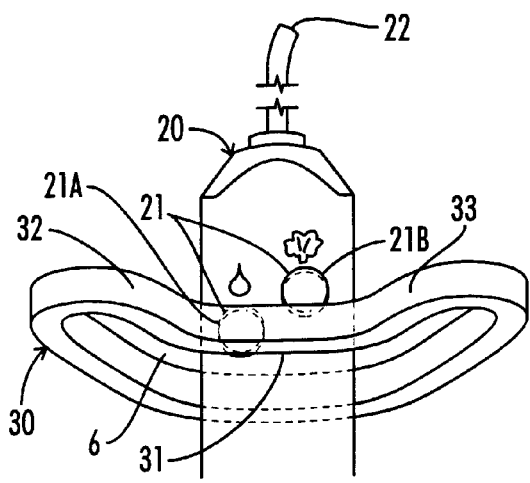
FIG. 10 is a top view of the device of FIG. 8 in combination with a euro-style syringe.
Figure 11:
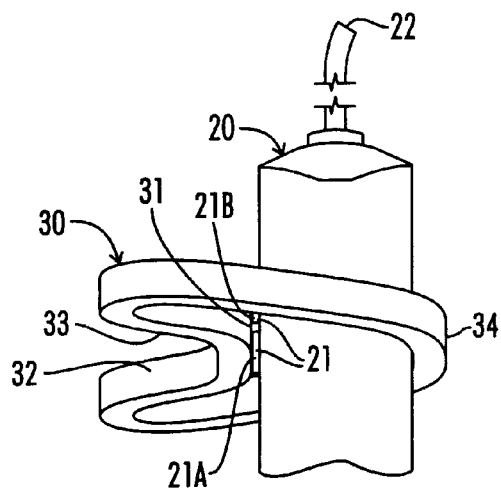
FIG. 11 is a side view of FIG. 10.

FIGS. 10 and 11 depict hold-down device 30 in combination with euro-style syringe 20, wherein flattened portion 31 depresses one or more buttons 21 on syringe 20. Button depression is caused by the spring-like action of biasing wings 32 and 33, which are those portions of hold-down device 30 that extend away from flattened portion 31. Biasing wings 32 and 33 preferably form minor curves in the loop such that a top view of hold-down device 30 resembles an inverted A-shaped or boomerang-shaped loop. Biasing wings 32 and 33 also connect flattened portion 31 to bracing portion 34. The wings and bracing portion act together to stably hold flattened portion 31 against one or more buttons 21 on syringe 20, in turn controlling the output from syringe tip 22. It can be seen in FIG. 11 that the inner flat area of bracing portion 34 fits securely against the flat surface of euro-style syringe 20.

Figure 9:
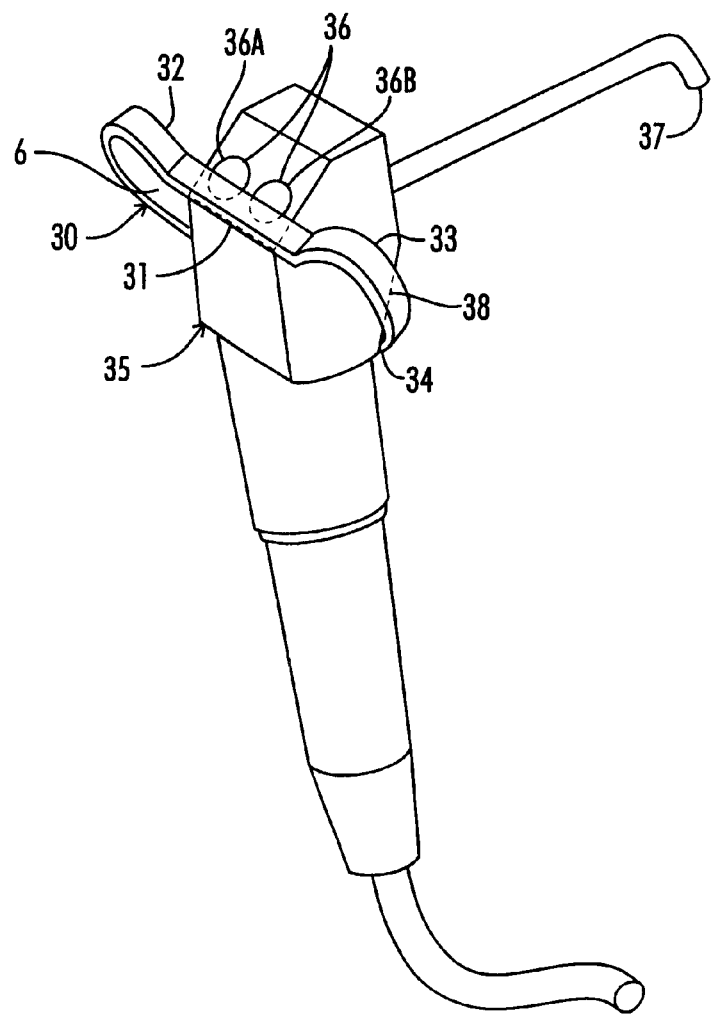
FIG. 9 is the device of FIG. 8 in combination with a standard dental syringe.
Figure 12:
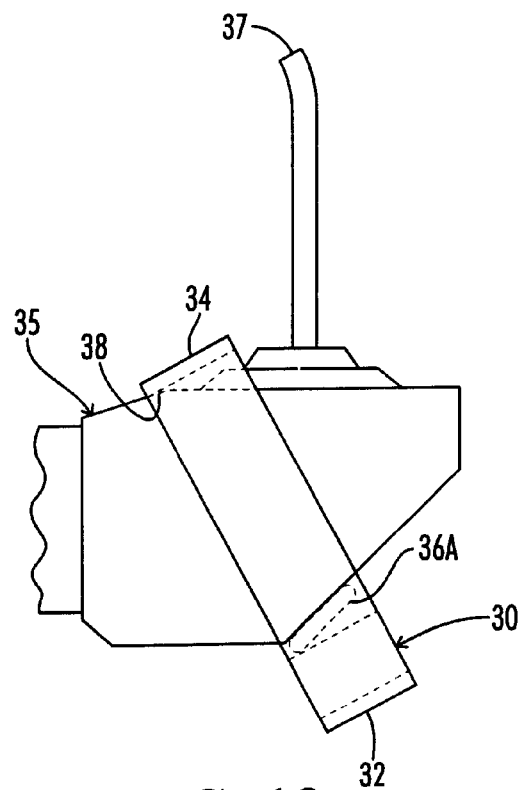
FIG. 12 is a side view of FIG. 9.

FIGS. 9 and 12 are perspective and side views, respectively, of hold-down device 30 in combination with standard dental syringe 35, wherein flattened portion 31 of hold-down device 30 holds down and depresses one or more buttons 36A and 36B on syringe 35 to control the flow of water through syringe tip 37 of syringe 35. Bracing portion 34 of hold-down device 30 engages the forward portion 38 of syringe 35 and supports flattened portion 31 in place on syringe 35.

Installing hold-down device 30 on either the euro-style syringe of FIGS. 10 and 11 or the standard dental syringe of FIGS. 9 and 12 is performed by inserting syringe tip 22 or syringe tip 37, respectively, forwardly through opening 6 in hold-down device 30, then simultaneously securing bracing portion 34 and hold-down portion 31 around euro-style syringe 20 or standard dental syringe 35, respectively, so that hold-down portion 31 holds down at least one of buttons 21A and 21B on euro-style syringe 20, or at least one of the buttons 36A and 36B on standard dental syringe 35, respectively. Installing hold-down device 30 on either the euro-style syringe of FIGS. 10 and 11 or the standard dental syringe of FIGS. 9 and 12 in this manner will relieve the user of the need to attend the combination, freeing the user to perform other tasks during purging.

It can be seen in FIG. 12 that bracing portion 34 engages the forward portion 38 of standard dental syringe 35 at an angle, not on an equal plane. While embodiments could be devised incorporating a bracing portion that fits flush against the forward portion of the dental syringe, it is unnecessary to do so in the practice of the invention as described herein. It is sufficient for bracing portion 34 to contact standard dental syringe 35 as shown in FIG. 12 or in any manner to stably support hold-down device 30 in combination with standard dental syringe 35. In such combination, biasing members 32 and 33 act as springs to cause flattened portion 31 to continually depress at least one of buttons 36A and 36B on standard dental syringe 35.

The device of FIG. 8 could alternatively be described as an endless semi-rigid flexible loop having first and second diverging side portions 32 and 33, respectively, that are connected to a horizontal cross piece 31 and diverge away from the cross piece, turning inwardly to form hold-down wings 32 and 33. Hold-down wings 32 and 33 join at a vertex 34 in the part of the loop opposite horizontal crosspiece 31, which holds down at least one of buttons 21A and 21B on euro-style syringe 20 as in FIGS. 10 and 11, or at least one of buttons 36A and 36B on standard dental syringe 35 as in FIGS. 9 and 12.

The device of FIG. 8 could further be described as having an inner first surface 31 for holding down at least one of the buttons 21A or 21B on euro-style syringe 20 as in FIGS. 10 an 11, or for holding down at least one of the buttons 36A and 36B on standard dental syringe 35 as in FIGS. 9 and 12. The device in FIG. 8 could further be described as having an inner second surface 34 for bracing hold-down device 30 against either euro-style syringe 20 as in FIGS. 10 an 11, or against standard dental syringe 35 as in FIGS. 9 and 12. Hold-down device 30 could further be described as having first biasing member 32 and second biasing member 33 opposingly extending from opposite ends of inner first surface 31 for biasing inner first surface 31 against at least one of the buttons 21A or 21B on euro-style syringe 20 as in FIGS. 10 an 11, or at least one of the buttons 36A and 36B on standard dental syringe 35 as in FIGS. 9 and 12. In such configuration, first biasing member 32 and second biasing member 33 also serve to connect inner first surface 31 to inner second surface 34 at a distance sufficient to cause inner first surface 31 and inner second surface 34 to simultaneously engage standard dental syringe 35 or euro-style syringe 20.

When hold-down device 30 is in place on either euro-style syringe 20, as in FIGS. 10 and 11, or on standard dental syringe 35, as in FIGS. 9 and 12, the combination could be described as a syringe in combination with a purge loop, wherein the purge loop comprises a first inner surface 31 engaging water discharge button 21A on euro-style syringe 20, or engaging water discharge button 36A on standard dental syringe 35. A second inner surface 34 engages the surface of euro-style syringe 20 opposite water discharge button 21A or the surface of standard dental syringe 35 opposite water discharge button 36A. Hold-down device 30 as herein described further comprises a first side member 32 and a second side member 33 that extend distally of (or away from) second inner surface 34 to connect first inner surface 31 and second inner surface 34.

Figure 13:
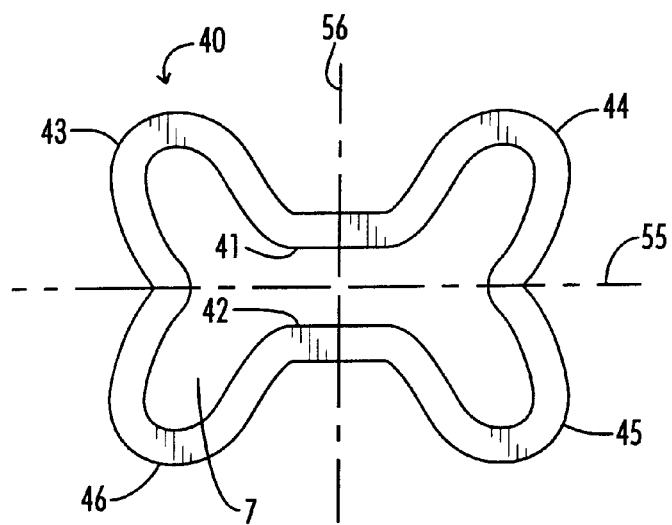
FIG. 13 is a top view of a butterfly-shaped syringe purge loop.

FIG. 13 is another embodiment of the hold-down device of the instant invention. FIG. 13 shows a butterfly-shaped continuous loop 40 of the same manufacture as previously-discussed embodiments. Hold-down device 40 is symmetric about axes 55 and 56, comprising two flattened portions 41 and 42, and four biasing members 43, 44, 45, and 46 that define resilient spring loops acting to force flattened portions 41 and 42 toward each other.

Further with respect to hold-down device 40, flattened portion 41 acts in the same biasing manner as hold-down portion 11 in hold-down device 10 (FIGS. 1, 3, 4, 6, and 7), and in the same biasing manner as hold-down portion 31 in hold-down device 30 (FIGS. 8–12). Similarly, flattened portion 42 acts in the same bracing manner as bracing portion 12 in hold-down device 10 (FIGS. 1, 3, 4, 6, and 7), and in the same bracing manner as bracing portion 34 in hold-down device 30 (FIGS. 8–12).

When hold-down device 40 is installed on a syringe, the two lower of biasing members 43, 44, 45, and 46 may also act as legs for supporting the hold-down device/syringe combination on a surface. When so supported, the hold-down device/syringe combination would not need to be held by the user; rather, the combination would be able to be left alone during purging. Hold-down device 40 has an added benefit to previously-discussed embodiments. Unlike the foregoing, it can be concluded from FIG. 13 that it is impossible to install hold-down device 40 upside down on a dental syringe. Due to the symmetry of hold-down device 40 as described above, hold-down device 40 may be easily inverted about axis 55 or axis 56 without consequence.

Figure 14:
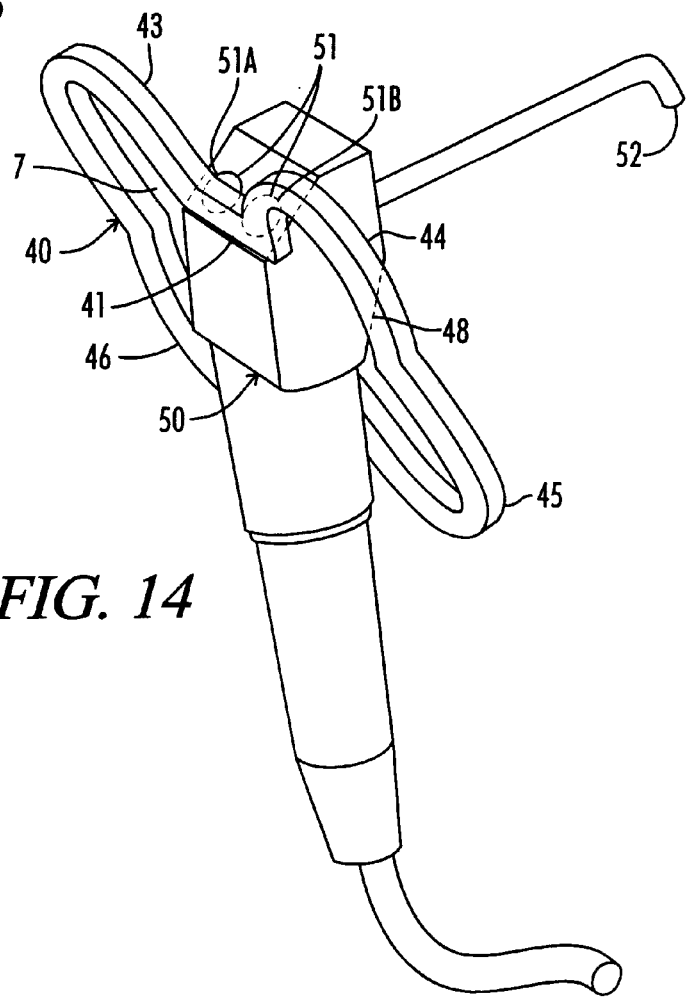
FIG. 14 is the device of FIG. 13 in combination with a standard dental syringe.
Figure 15:
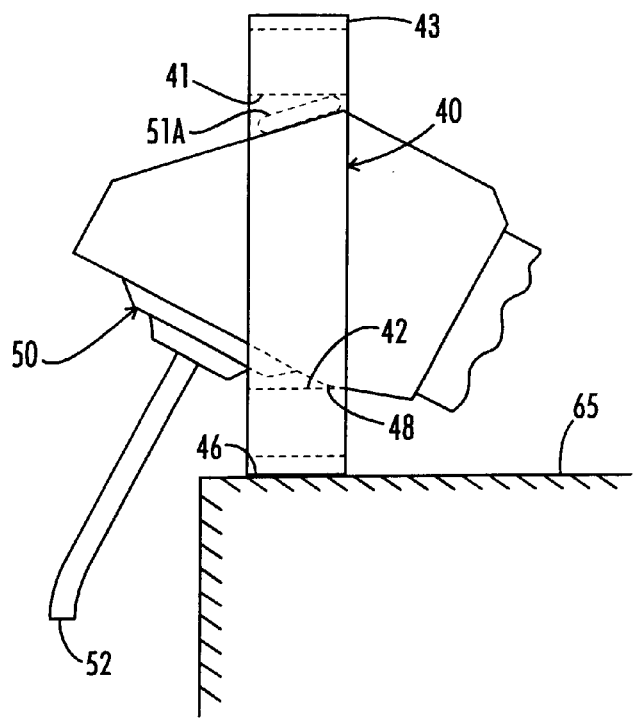
FIG. 15 is a side view of FIG. 14.

FIGS. 14 and 15 depict perspective and side views of a known standard dental syringe 50 having one or more buttons 51A and 51B controlling output of air and water from syringe tip 52, in combination with device 40 having flattened portion 41 continually depressing one or more buttons 51A and 51B of syringe 50 by biasing members 43 and 44, and biasing members 45 and 46 serve the complementary function of supporting the combination of device 40 with standard dental syringe 50 and further biasing flattened portion 42 against the forward area 48 of standard dental syringe 50. Biasing members 45 and 46 have the above-discussed additional feature of supporting the combination on a surface 65 in FIG. 15.

It can be seen in FIG. 15 that bracing portion 42 engages the forward portion 48 of standard dental syringe 50 at an angle, not on an equal plane. While embodiments could be devised incorporating a bracing portion that fits flush against the forward portion of the dental syringe, it is unnecessary to do so in the practice of the invention as described herein. It is sufficient for bracing portion 42 to contact standard dental syringe 50 as shown in FIG. 15 or in any manner to stably support hold-down device 40 in combination with standard dental syringe 50. In such combination, biasing members 43 and 44 act as springs to cause flattened portion 41 to continually depress at least one of buttons 51A and 51B on standard dental syringe 50.

Figure 16:
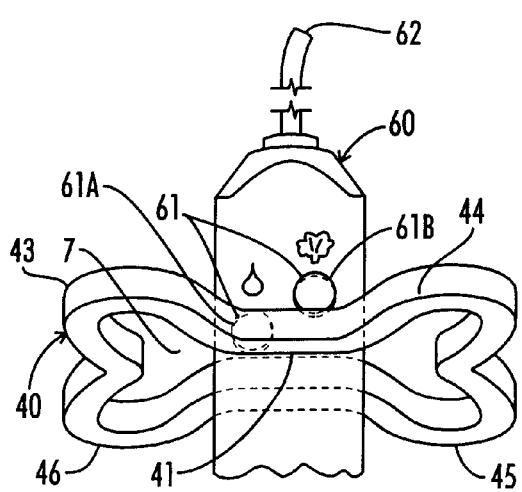
FIG. 16 is a top view of the device of FIG. 13 installed in combination with a euro-style syringe.
Figure 17:
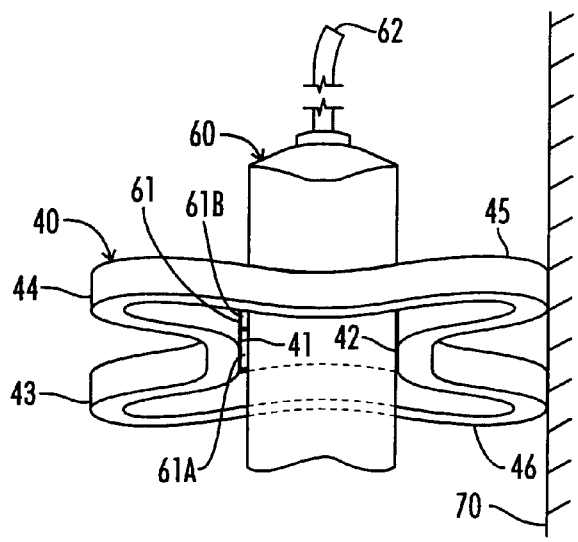
FIG. 17 is a side view of FIG. 16.

FIGS. 16 and 17 illustrate top and side views of device 40 installed on eurostyle syringe 60. Device 40 is installed in the same manner as discussed above relating to FIGS. 14 and 15, with flattened portion 41 of device 40 depressing one or more buttons 61 of euro-style syringe 60 to control the output of water and/or air from syringe tip 62 biasing members 43 and 44 act to hold flattened portion 41 against one or more buttons 61 of syringe 60 and biasing members 45 and 46 of device 40 serve to bias and support the combination as legs on a surface 70 in FIG. 17. It can be seen in FIG. 17 that the inner flat area of bracing portion 42 fits securely against the flat surface of euro-style syringe 60.

Installing hold-down device 40 on either the standard dental syringe of FIGS. 14 and 15 or the euro-style syringe of FIGS. 16 and 17 is performed by inserting syringe tip 52 or syringe tip 62, respectively, forwardly through opening 7 in hold-down device 40, then simultaneously securing bracing portion 42 and hold-down portion 41 around standard dental syringe 40 or euro-style syringe 60, respectively, so that hold-down portion 41 holds down at least one of buttons 51A and 51B on standard dental syringe 50, or at least one of the buttons 61A and 61B on euro-style syringe 60, respectively.

Several methods of practicing the invention are herein described. One method of practicing the invention is first biasing an object against one or more discharge buttons on a dental syringe, then bracing the object against the body of the dental syringe such that the buttons are continuously depressed. Additionally, the combination of the object depressing the buttons and the syringe can be supported on a surface. Another method of practicing the invention is to place a semi-rigid, non-round loop around a dental syringe such that a first portion of the loop engages one or more buttons on the syringe, and such that a second portion of the loop braces the loop against the syringe while maintaining sufficient tension to cause the first portion to continually hold down the one or more buttons on the syringe.

Thus it is seen that the apparatus and methods of the present invention readily achieve the ends and advantages mentioned, as well as those inherent therein. While certain preferred embodiments have been illustrated and described for purposes of the present disclosure, numerous changes in parts and steps may be made by those skilled in the art, which changes are encompassed within the scope and spirit of the appended claims.

What is claimed is:

1. An apparatus for purging a dental syringe, comprising:
   a hold-down portion for holding down one or more buttons on the syringe; and
   a bracing portion for stably holding the hold-down portion against one or more buttons on the syringe.

2. An apparatus as in claim 1, wherein the hold-down portion and the bracing portion are made of a single molded piece.

3. An apparatus as in claim 2, wherein the single molded piece is semi-rigid.

4. An apparatus as in claim 3, wherein the single molded piece is made of plastic.

5. An apparatus as in claim 1, wherein the hold-down portion further comprises a flat portion for engaging the one or more buttons, and two biasing members for biasing the flat portion against the one or more buttons.

6. An apparatus as in claim 5, wherein the biasing members opposingly extend from the hold-down portion.

7. An apparatus as in claim 6, wherein the biasing members connect the hold-down portion and the bracing portion.

8. An apparatus as in claim 1, further comprising a support portion proximate the bracing portion for stably supporting the apparatus on a surface.

9. An apparatus as in claim 8, wherein the support portion further comprises at least one leg extending from the bracing portion to the surface.

10. A purge hold down loop for a dental syringe, comprising an endless semi-rigid flexible loop having first and second diverging side portions joined at a vertex, the side portions each turning inwardly to define two hold-down wings, and a horizontal cross piece joining the hold-down wings, for holding down at least one button on the syringe.

11. An apparatus for purging a dental syringe, comprising:
    an inner first surface for holding down at least one button on the syringe;
    an inner second surface for bracing the apparatus against the syringe; and
    a first biasing member and a second biasing member opposingly extending from either side of the inner first surface for biasing the inner first surface against the button on the syringe, the first biasing member and the second biasing member further connecting the inner first surface to the inner second surface at a distance sufficient to cause the inner first surface and the inner second surface to simultaneously engage the syringe.

12. An apparatus for purging a dental syringe, comprising a loop having a flattened hold-down portion for holding down one or more buttons of the syringe, a bracing portion for stably holding the hold-down portion against the syringe buttons, and two side portions connecting the hold-down portion and the bracing portion.

13. An apparatus as in claim 12, wherein the loop is semi-rigid.

14. An apparatus as in claim 13, wherein the loop is made of acrylic.

15. A dental syringe and purge loop combination comprising:
  a dental syringe having at least one water discharge button for discharging water from the syringe; and
  a purge loop surrounding the syringe and continuously depressing the water discharge button.

16. A syringe and purge loop combination as in claim 15, wherein the purge loop further comprises a first inner surface that engages the water discharge button, a second inner surface engaging the syringe opposite the first inner surface, a first side member and a second side member connecting the first inner surface and second inner surface.

17. A syringe and purge loop combination as in claim 16, further comprising a biasing structure supportingly biasing the first inner surface against the water discharge button.

18. A syringe and purge loop combination as in claim 17, wherein the biasing structure comprises a first biasing portion and a second biasing portion connecting the first inner surface and the second inner surface.

19. A syringe and purge loop combination as in claim 18, wherein the first biasing portion and second biasing portion extend distal the second inner surface.

20. A syringe and purge loop combination as in claim 19, wherein the purge loop is an inverted A-shaped loop.

21. A syringe and purge loop combination as in claim 20, wherein the purge loop is boomerang-shaped.

22. A method of purging a dental syringe, comprising:
  biasing an object against one or more discharge buttons on the syringe; and
  bracing the object against the syringe body such that the buttons are continuously depressed.

23. The method of claim 22, further comprising the step of supporting the syringe on a surface while the object depresses the buttons.

24. A method of purging a dental syringe, comprising:
  placing a semi-rigid, non-round loop around the syringe such that a first portion of the loop engages one or more buttons on the syringe, and such that a second portion of the loop braces the loop against the syringe while maintaining sufficient tension to cause the first portion to continually hold down the one or more buttons on the syringe.

* * * * *